United States Patent [19]

Afonso et al.

[11] Patent Number: 5,506,236
[45] Date of Patent: Apr. 9, 1996

[54] 4-SUBSTITUTED PYRAZOLOQUINOLINE DERIVATIVES

[75] Inventors: Adriano Afonso, West Caldwell; Joseph M. Kelly, Parlin; Samuel Chackalamannil, East Brunswick, all of N.J.

[73] Assignee: Schering Corporation

[21] Appl. No.: 234,742

[22] Filed: Apr. 28, 1994

[51] Int. Cl.$^6$ .................. A61K 31/435; C07D 471/04
[52] U.S. Cl. .................................. 514/293; 546/82
[58] Field of Search ........................ 546/82; 514/293

[56] References Cited

U.S. PATENT DOCUMENTS

| | | | |
|---|---|---|---|
| 3,600,393 | 8/1971 | Graeve et al. | 546/82 |
| 3,790,576 | 2/1974 | DeWald | 546/82 |
| 4,013,665 | 3/1977 | Crenshaw | 546/82 |
| 4,757,088 | 7/1988 | Haines | 514/563 |
| 4,920,128 | 4/1990 | Bell | 514/293 |

OTHER PUBLICATIONS

Crenshaw et al., Journal of Medicianl Chemistry, 1976, vol. 19, No. 2, pp. 262–275.
Czechoslovak Pharmacy 34(3–4) pp. 119–122 (1985) and English translation thereof.

Primary Examiner—Ceila Chang
Attorney, Agent, or Firm—Matthew Boxer

[57] ABSTRACT

The invention relates to compounds represented by formula 1a or 1b

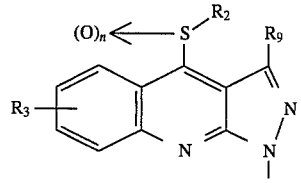

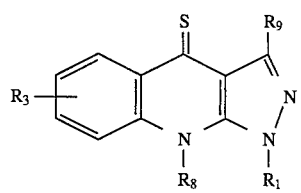

and pharmaceutically acceptable salts thereof wherein $R_1$, $R_2$, $R_3$, $R_8$, $R_9$, and n are as described herein.

These compounds are useful as agents in treating herpes virus infections.

12 Claims, No Drawings

4-SUBSTITUTED PYRAZOLOQUINOLINE DERIVATIVES

BACKGROUND OF THE INVENTION

This invention relates to 4-thiosubstituted 3-alkylpyrazolo[3,4-b]quinoline compounds, pharmaceutical compositions containing them and methods of treating patients afflicted with a herpes group virus infection by use of such compositions.

There are four separate herpes group viruses which infect and cause disease in humans. These four viruses are (1) the herpes simplex virus types 1 and 2 (HSV-1 and HSV-2, respectively); (2) the cytomegalovirus (CMV); (3) varicella-zoster (VZ) virus ;and (4) the Epstein-Barr (EB) virus.

Examples of diseases associated with HSV-1 and HSV-2 infections include herpes labialis, genital herpes (herpes progenitalis), neonatal herpes, herpetic keratitis, eczema herpecticum, disseminated herpes, occupational herpes, herpectic gingivostomatitis, meningitis (aseptic), and encephalitis.

The VZ virus is associated with chicken-pox (varicella) and shingles (zoster)in humans.

The CMV is wide spread in humans and numerous other mammals. A great majority of human CMV infections are subclinical; that is, the primary infection occurs with no signs or symptoms. An exception to this is a congenital infection which occassionally gives rise to cytomegalic inclusion body disease in infants. There is also a mononucleosis-like syndrome caused by the virus.

A great majority of serious cases due to CMV infections come from recurring infections in immuno-compromised individuals, such as in transplant patients and in cancer patients. It has been estimated that silent CMV infections have occurred in a majority of humans be the time adulthood is reached.

Examples of drugs used to treat herpes infections include: (1) IUDR (5'-iodo-2'-deoxyuridine); (2) Ara-C (1-[beta-D-arabinofuranosyl] -cytosine); (3) Ara-A (9-beta-D-arabinofuranosyladenine); and (4) Acyclovir (9-[(2-hydroxyethoxy)methyl] guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of panthothenic acid or its alcohol and salt forms, dexpanthenol and pantothenate, respectively, to lidocaine or lidocaine hydrochloride significantly enhances and antiviral activity of those drugs.

There is still a need for antiviral compounds exhibiting activity against the herpes group viruses, especially against HSV-1 and HSV-2.

SUMMARY Of THE INVENTION

The present invention provides compounds represented by formulas 1a and 1b

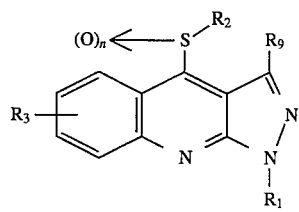

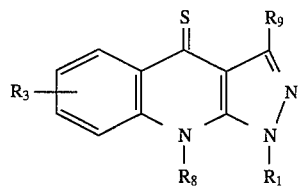

and pharmaceutically acceptable salts thereof, wherein $R_1$ is H, $(C_2–C_8)$alkanoyl,

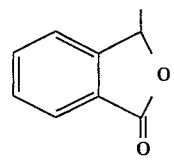

or $-CH_2O-(C_2–C_8)$alkanoyl $R_2$ is H, $(C_1–C_8)$alkyl, $(C_2–C_8)$alkanoyl, $-(C_2–C_6)$alkylene, or $-S-(CH_2)_q-N(R_4)_2-$;

$-(CHR_4)_S-N(R_5)_2$, $-(CHR_4)_S-CO_2M$,

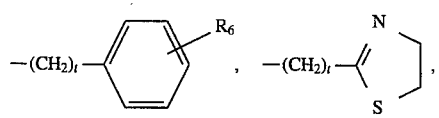

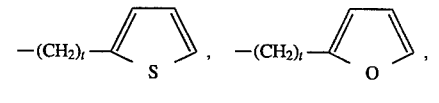

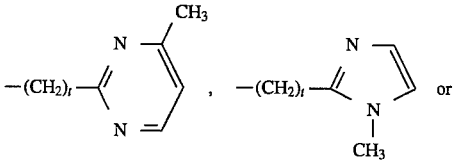

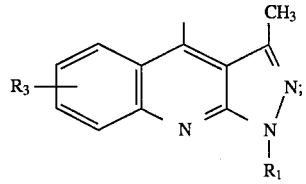

$R_3$ is $OR_5$, F, Cl, Br, I, $CF_3$ or, $(C_1–C_8)$alkyl;

$R_4$ is H or $(C_1–C_8)$alkyl;

$R_5$ is H, $(C_1–C_8)$alkyl or $(C_2–C_7)$alkanoyl;

$R_6$ is $R_3$, $N(R_5)_2$, $(C_2–C_7)$alkanoyl or H;

$R_8$ is $R_5$ or

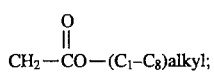

$R_9$ is $(C_1-C_8)$alkyl;
M is H or a pharmaceutically acceptable cation;
n is 0 or 1;
q is 2 or 3;
s is 1, 2, 3 or 4; and
t is 0, 1, 2 or 3.

In a preferred embodiment, the present invention provides compounds represented by formula 2

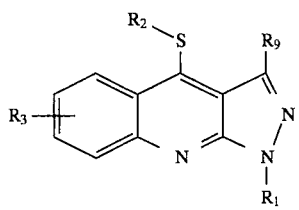

and pharmaceutically acceptable salts thereof, wherein $R_1$ is H, $(C_2-C_8)$alkanoyl,

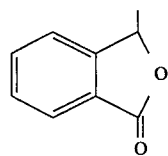

or $-CH_2O-(C_2-C_8)$alkanoyl)

$R_2$ is H, $(C_1-C_8)$alkyl, $(C_2-C_8)$alkanoyl, $-(C_2-C_6)$alkylene, $-(CHR_4)_s-N(R_5)_2$, $-(CHR_4)_s-CO_2M$,

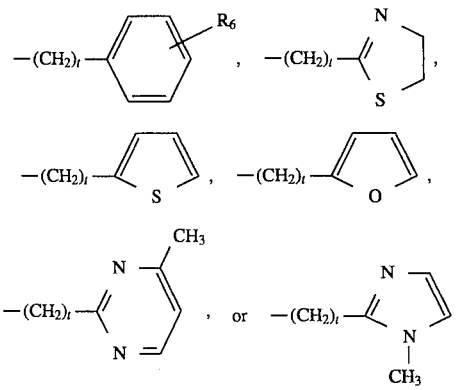

$R_3$ is $OR_5$, F, Cl, Br, I, $CF_3$ or, $(C_1-C_8)$alkyl,
$R_4$ is H or $(C_1-C_8)$alkyl;
$R_5$ is H, $(C_1-C_8)$alkyl or $(C_2-C_8)$alkanoyl;
$R_6$ is $R_3$, $N(R_5)_2$, $(C_2-C_7)$alkanoyl or H;
$R_8$ is $R_5$ or

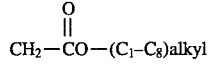

$R_9$ is $(C_1-C_8)$alkyl;
M is H or a pharmaceutically acceptable cation;
q is 2 or 3;

s is 1, 2, 3, or 4; and
t is 0, 1, 2, or 3.

Also preferred are compounds of formulas 1a and 1b wherein $R_3$ is $6-(C_1-C_8)$alkyl-O-.

Also preferred are compounds of formulas 1a and 1b wherein $R_9$ is $CH_3$-.

Also preferred are compounds of formulas 1a and 1b wherein $R_3$ is $6-CH_3-O-$.

Also preferred are compounds of formulas 1a and 1b wherein $R_3$ is H.

Also preferred are compounds of formulas 1a wherein $R_2$ is

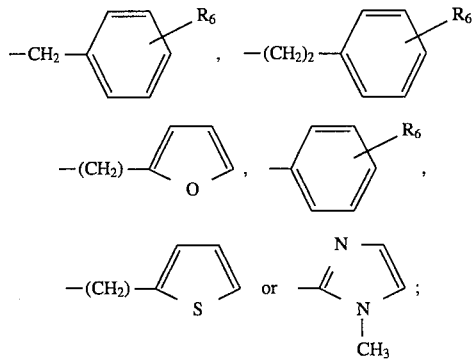

$R_1$ is H or

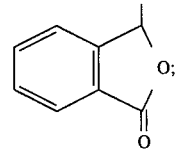

and n is 0

Also preferred are compounds of formula 1a wherein $R_2$ is

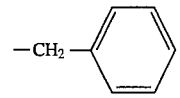

and $R_3$ is $6-CH_3O$

Also preferred are compounds of formula 1a wherein $R_2$ is

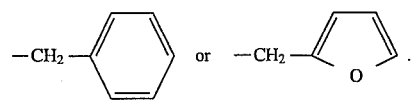

The most preferred compounds of the invention are

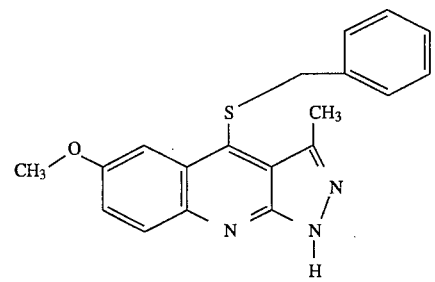

and

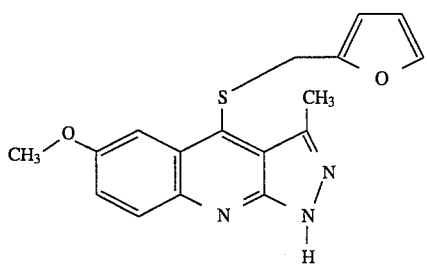

Other compounds of the invention are of the formula

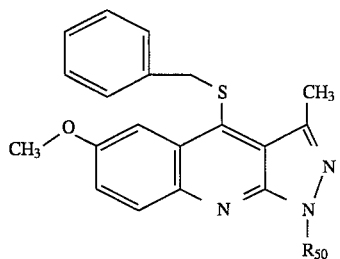

wherein $R_{50}$ is the residue of an α-amino acid.

One such compound of the invention is

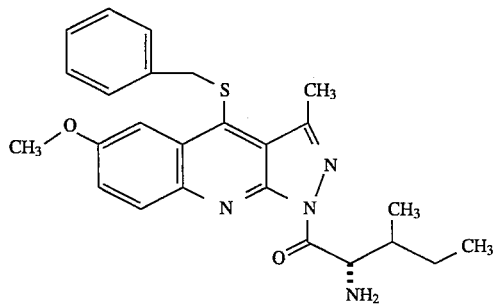

or a pharmaceutically acceptable salt thereof.

The compound of formula (30) just above has a FAB MASS SPECTRUM of 449 $(M+1)^+$.

The present invention also provides pharmaceutical compositions for treating patients afflicted with a herpes group virus which comprises an anti-herpes effective amount of a compound of formulas 1 a, 1 b or 2 and a pharmaceutically acceptable carrier therefor as well as methods of treating a patient afflicted with a herpes group virus which comprises administering to said patient an anti-herpes effective amount of a compound of formulas 1a, 1b, (30) just above or 2.

DETAILED DESCRIPTION OF THE INVENTION

The term "$(C_1-C_8)$ alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso-, tert-hexyl and n-, sec-, iso-, tert-, and neo-heptyl and n-, sec-, iso-, tert-, and neo-octyl. The preferred $(C_1-C_8)$alkyl is methyl.

The term "$(C_2-C_8)$ alkanoyl" refers to straight and branched chain alkanoyl groups having 2 to 8 carbon atoms such as acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. Acetyl is preferred.

The term "$(C_2-C_6)$ alkylene" refers to straight and branched chain alkylene groups of 2 to 6 carbons including $-C_2H_3$, $-C_3H_5$ $-C(CH_3)=CH_2$, $-C_4H_7$, $-CH_2-C(CH_3)=CH_2$, $-C_5H_9-$, $-C_6H_{11}-$ and $-(CH_2)_2-C(CH_3)=CH_2$.

The term "pharmaceutically acceptable cation" refers to sodium, calcium, and potassium ions.

The term "pharmaceutically acceptable salt" refers to maleates, hydrochlorides, hydrobromides, sulfates, phosphates and tartrates. On skilled in the art will realize that acid additon salts of the compounds of the invention may be made with such salts whenever a basic functionality is present in a particular compound of the invention.

The term "residue of an α-amino acid" means an α-amino acid which lacks an OH group on the carboxyl group of the amino acid. Such an α-amino acid is bonded by means of a peptide bond through the carboxyl group directly to the nitrogen atom at the 1-position of the pyrazoloquinoline ring. An example of a residue of an α-amino acid is found in compound (30) shown just below and is indicated by the arrow:

(30)

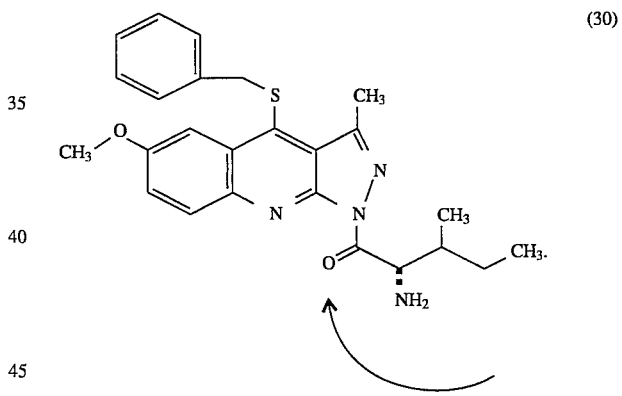

Exemplary of α-amino acids are glycine, alanine, valine, leucine, isoleucine, phenylalanine, proline, serine, threonine, tyrosine, cysteine, cystine, methionine, aspartic acid, glutamic acid, asparagine, glutamine, tryptophan, lysine, arginine, and histidine.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

SCHEME 1
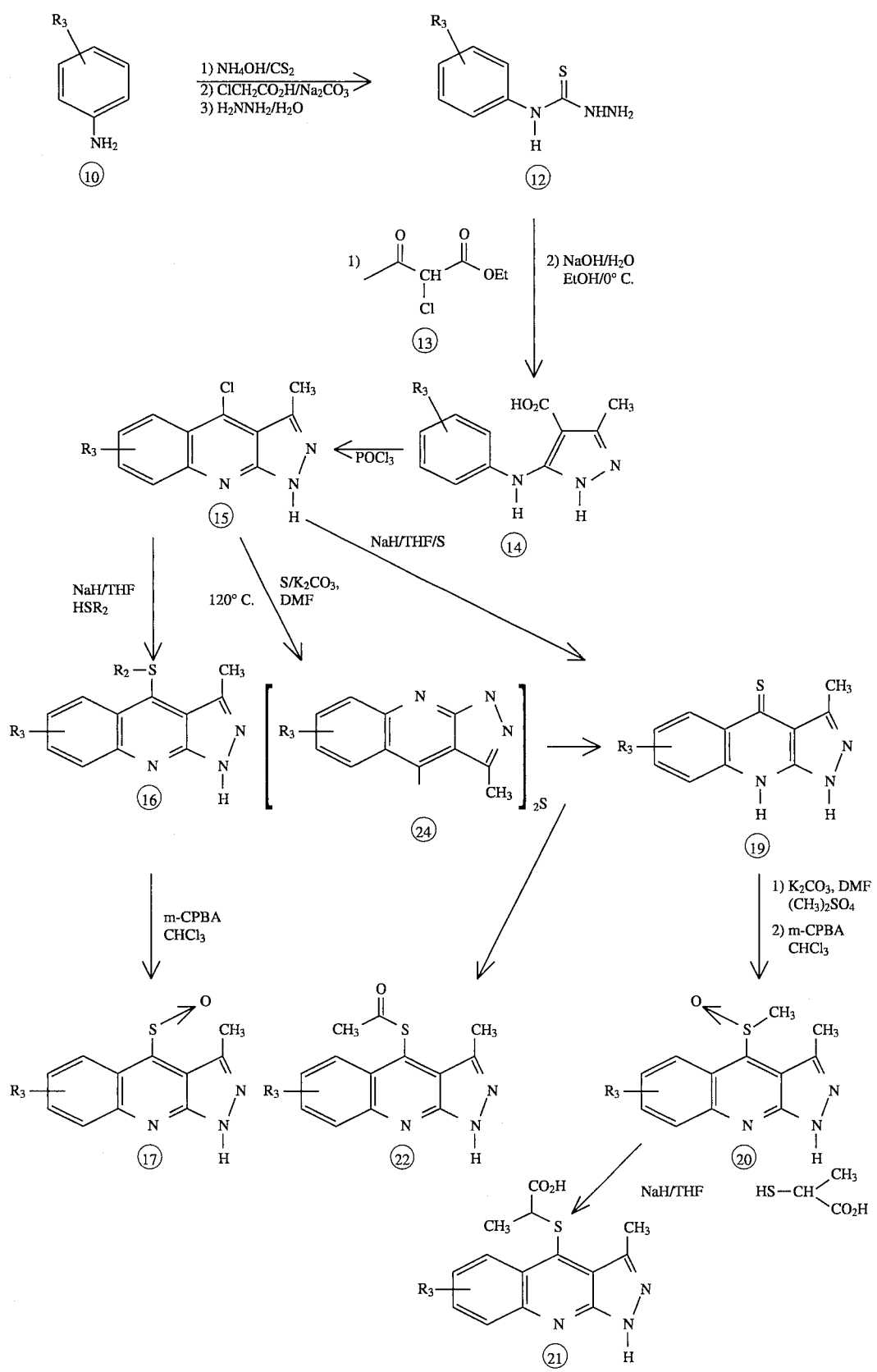

The compounds of the present invention wherein $R_9$ is $CH_3$ may be prepared in accordance with the sequence of steps outlined in Scheme I and the Examples hereinbelow. The synthetic schemes uses as starting materials the commercially substituted anilines 10. Reaction of 10 to form 12 is conveniently performed in accordance with the procedures of Radl, S et. al. *Coll. Czech. Chem. Commun*, (1986), Vol. 51, 1692.

Reagents (1) carbon disulfide and ammonia, (2) chloroacetic acid, sodium salt and (3) hydrazine hydrate are sequentially reacted with 10 to afford the thiosemicarbazide 12. Cyclization of 12 with ethyl 2-chloroacetoacetate 13 in the presence of base, e.g. ethanolic sodium hydroxide provided the pyrazole derivative (not shown). Saponification of the pyrazole derivative in aqueous ethanolic sodium hydroxide at reflux provided the free acid 14. The acid 14 was cyclized with $POCl_3$ to provide the 4-chloropyrazolo [3,4-b] quinoline 15. Reaction of 15 with strong base (e.g. NaH) and mercaptan $R_2SH$ in an aprotic solvent, e.g. THF provided the 4-thio derivatives 16. The mercaptans $R_2SH$ are commercially available, e.g. from Aldrich Chemical Co. Wilwaukee, Wisc. Selective oxidation of 16 with, for example, m-chloroperbenzoic acid (m-CPBA) produced the sulfoxide 17. Reaction of 15 with sulfur and base (e.g., potassium carbonate)in DMF produced dimer 24. Reaction of the 4-chloro-compound 15 with strong base (e.g. NaH) and sulfur in an aprotic solvent (e.g., THF) produced the 4-thio compound 19. Reaction of 19 with acetic anhydride at low temperatures under basic conditions produced the 4-alkanoylthio-compound 22. Reaction of 19 with dimethyl sulfate and base (e.g., $K_2CO_3$) produced the sulfenyl compound (not shown) which was oxidized to the sulfinyl compound 20 by use of a selective oxidizing agent (e.g., m-CPBA). Reaction of 20 with mercaptans $R_2SH$ such as $CH_3CH(CO_2H)SH$ in strong base (e.g. NaH) and aprotic solvents' (DMF/THF) produced 4-thio-compounds 21.

The compunds of the present invention wherein $R_9=(C_2-C_8)$alkyl may be prepared in accordance with Scheme I by substitution of

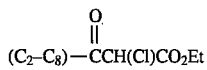

for ethyl-2-chloroacetoacetate 13 in Scheme I or in Example 2.

The compounds of this invention exhibit anti-HSV activity in two art recognized in vitro assays: (1) a βeta Galactosidase Assay and (2) a Plaque Reduction Assay. $IC_{50}$ values for the compounds of this invention in each assay were in the range of 1.0 to <10 µg/mL.

The compound (30) of this invention exhibits anti-HSV activity at 0.5 µg/mL in (1) a βeta Galactosidase Assay; and at 0.2 µg/mL in (2) a Plaque Reduction Assay.

IN-VITRO ANTI-HSV ACTIVITY ASSAYS

1. Transient Expression Assay for Effects Against HSV Early Gene Expression (βeta Galactosidase Assay)

Cultured HeLa cells are seeded onto 96-well assay plates and allowed to reach ~90% confluency by incubation at 37° C. for 24 hours. The resulting monolayers are transfected with an expression plasmid containing the *Escherichia coil* lacZ gene, which encodes for the enzyme β-galactosidase, under control of the HSV-1 tk promoter. Transfected cells are allowed to recover by incubation at 37° C. for 48 hours. Test compounds are diluted in cell culture media, containing a fixed percentage of DMSO, to generate a range of concentrations spanning 2 logs. Monolayers are infected with HSV-2 in the presence, and as control the absence, of test compound at 37° C. for 18 hours. Following incubation the monolayers are washed in phosphate buffered saline and cells are lysed in the presence of detergent. β-galactosidase activity is determined by incubation of an aliquot of each lysate with the methyl umbelliferyl galactosidase (MUG) substrate which is enzymatically cleaved to generate a fluorescent product. Fluorescence is quantitated on a Dynatech micofluorimeter. The inhibitory activity of a compound is plotted versus concentration and is expressed as an $IC_{50}$ value, i.e., that concentration which reduces the beta glactosidase expression as shown by the fluorescent signal to 50% of that produced by infected but untreated cells.

2. Plaque Reduction Assay for HSV Antiviral Activity

Cultured Vero cells are seeded into 6-well cluster plates and allowed to reach confluency by incubation at 37° C. for 24 hours. Test compounds are diluted in cell culture media, containing a fixed percentage of DMSO, to generate a range of concentrations spanning 2 logs. Monolayers are infected with HSV-2 (MS) to a final concentration of 100 plaque forming units/well in the presence, and as control the absence, of test compound at 37° C. for 18 hours. Following incubation the monolayers are washed in phosphate buffered saline and overlayed with methylcellulose in culture medium. Monolayers are incubated at 37° C. for an additional 48 hours to allow formation of viral plaques. Viral plaques are visualized by aspiration of the overlay and staining of the monolayer with crystal violet, and subsequently counted. The plaque reduction activity of a compound of this invention expressed as an $IC_{50}$ value, i.e. that concentration which reduces the number of plaques to 50% of that produced in infected but untreated cells.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses rangling from about 0.1 mg/kg to abut 100mg/kg of body weight.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following examples are illustrative only and should not be construed as limiting the invention in any way. Those skilled in the art will appreciate that variations are possible which are within the spirit and scope of the appended claims.

Example 1

4-(4-Methoxyphenyl)Thiosemicarbazide (12a)

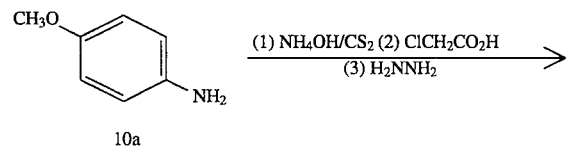

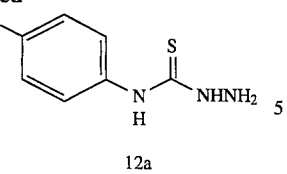

To a stirred solution of 4 methoxyaniline (36 g, 0.3 mol) in ethanol (100 mL) was added conc. aqueous ammonia (25 mL). To the stirred solution so-formed was added carbon disulfide (23 g, 0.3 mol) over a 15 minute period. Stir the solution at a temperature of 20° C. for 1 hour. To this solution, was added a solution formed by admixing chloroacetic acid (28.3 g, 0.3 mol) in water (60 mL) and sodium carbonate (16 g, 0.15 mol). Stir the so-formed mixture for 1 hour at 20° C. and add dropwise thereto hydrazine (80%, 22.5 mL, 0.36 mol). Stir the so-formed reaction mixture for 4 hours and store the reaction mixture in a refrigerator at 5° C. for 16 hours. Filter the insoluble solid, and wash the solid with ethanol (20 mL). Crystallize the crude solid in hot ethanol and collect the title compound in the form of a white crystalline solid (50.8 g, 86% of theory).

Example 2

3-(4-Methoxyanilino)-5-Methyl-1H-Pyrazole-4-Carboxylic Acid (14b)

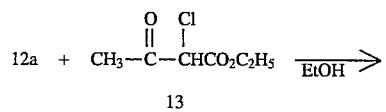

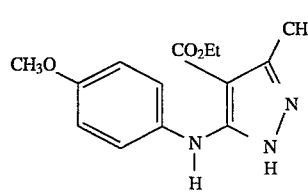

a) Ethyl-3-(4-Methoxyanilino)-5-Methyl-1(H) Pyrazolo-4-Carboxylate (14a)

Add a solution of ethyl 2-chloroacetoacetate (17 g, 0.10 mol) in ethanol (50 mL) at 20° C. to a stirred suspension in ethanol (100 mL) of the Compound 12a (19.7, 0.1 mol) prepared in accordance with Example 1. Stir the reaction mixture for 2 hours at room temperature and then place the reaction mixture in a refrigerator at 5° C. overnight. Collect the insoluble crude solid by filtration. Crystallize the solid in hot ethanol, remove the insoluble sulfur by filtration and collect the title compound (14a) of 2a in the form of yellow crystals (17 g). Concentrate the mother liquor/filtrate to a third of its original volume to produce an additional 30 g of yellow crystals of 14a, m.p. 152°–153°. (total yield 73%)

b) 3-(4-Methoxyanilino)-5-Methyl-1H-Pyrazole-4-Carboxylic Acid (14b)

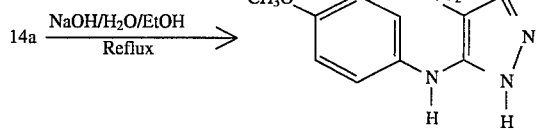

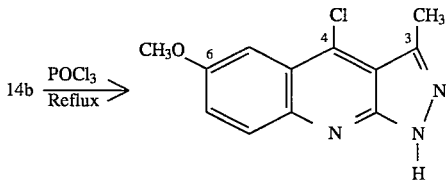

To a solution of compound 14a of Example 2a (7.2 g, 25 mmol) in ethanol (20 mL) at 50° C. was added a solution of NaOH (10 g) in water (125 mL). Heat the mixture so-formed at reflux for 6 hours. Cool the reaction mixture to 50° C., acidify with sufficient conc. hydrochloric acid to obtain a pH equal to 3. Collect the precipitated solid by filtration at room temperature. Wash the filtered solid with water and dry it at 60° C. and 0.2 mm Hg vacuum to produce the title compound (14b) as a white solid (5.4 g, 83% of theory).

Example 3

4-Chloro-6-Methoxy-3-Methyl-1H-Pyrazolo-[3,4-b]Quinoline (15a)

Heat a mixture of the compound 14b from Example 2b (7.8 g, 30 mmol) and phosphorous oxychloride (POCl$_3$) (100 mL) at 100° C. for 2 hours. Remove the POCl$_3$ at 50° C. and a vacuum of 30 mm Hg to produce a syrupy residue which was added dropwise to ice (200 g). Slowly, add 20% (W/W) NaOH in water to the stirred ice mixture. Remove the precipitated yellow solid by filtration and wash the solid with water (150 mL). Crystallize the washed solid from dimethylformamide (DMF)—water to produce the title compound (15a) as a yellow powder (6.1 g, 78% of theory).

Example 4

6-Substituted Derivatives of 4-Chloro-3-Methyl-1H-Pyrazolo[3,4-b]Quinoline (15a–d)

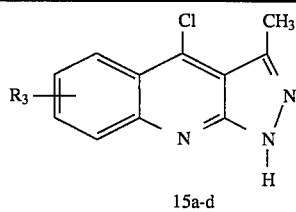

15a-d

| Example | A | R$_3$ |
|---|---|---|
| 4a | 4-fluoroaniline | 6-F— |
| 4b | p-toluidine | 6-CH$_3$— |
| 4c | 4-trifluoromethylaniline | 6-CF$_3$— |
| 4d | 4-chloroaniline | 6-Cl— |

Follow the procedure of Example 1 except substitute for 4-methoxyaniline an equivalent quantity of the commercially available substituted anilines listed in column A. Thereafter, follow the procedure of Examples 1 to 3 to obtain the compounds of formulas 15a–d wherein $R_3$ is as shown in the column labelled $R_3$.

Example 5

6-Methoxy-4-Thioxo-3-Methyl-1H-Pyrazolo[3,4-b]Quinoline

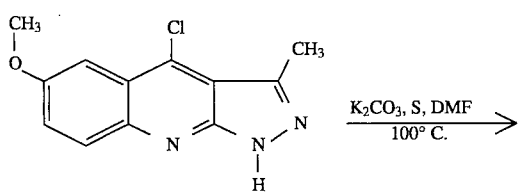

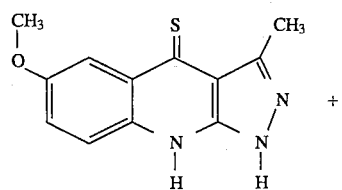

19a

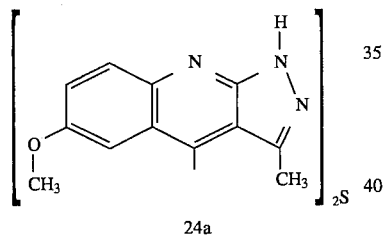

24a

Add anhydrous potassium carbonate ($7.24\times10^{-2}$M) to a solution of 4-chloro-6-methoxy-3-methyl-1$\underline{H}$ hydrozolo-[3,4-b] quinoline prepared in accordance with Example 3 (10 g, $4.0\times10^{-2}$M) and sulfur (4.0 g, $12.50\times10^{-2}$M) in anhydrous dimethylformamide (100 mL) at 70° C. Stir the so-formed reaction mixture for 15 hours at 100° C. Cool the reaction mixture to room temperature (20° C.), and filter the so-formed yellow precipitate. Wash the precipitate with water (100 mL). Purify the precipitated solid by recystallization from a dimethylformamide:water mixture to yield the dimeric product 24a as yellow crystals (3.6 g, 19.48% yield).

Mass spectrum (El) 456.1

Molecular Formula: $C_{24}H_{20}N_6O_2S$: Calc: C, 63.14%; H, 4.41%; N, 18.41%; Found: C, 62.80%; H, 4.40%, N, 18.34%

Acidify the mother liquors with 1$\underline{N}$ HCl to provide a precipitate, which was filtered, washed with water (100 mL), recrystallized from a dimethylformamide:water mixture and dried (60° C., 0.2 mm) to yield the title compound 19a (6.0 g, 60%). M.S. (El, M$^+$) 245 Molecular Formula $C_{12}H_{11}N_3OS$: Calc: C, 58.53%; H, 4.56% N, 14; Found: C,

Example 6

6-Methoxy-4-Methylthio-3-Methyl-1H-Pyrazolo[3,4-b]Quinoline (16a)

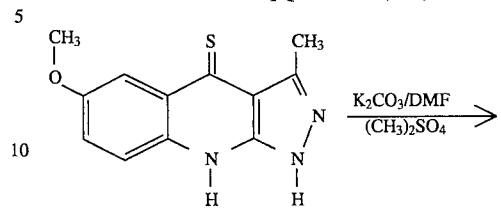

19

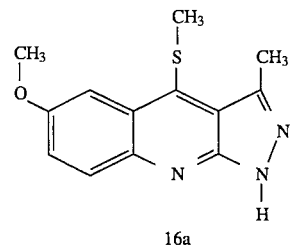

16a

Add anhydrous potassium carbonate (50 mg, 0.362 mmol) to a solution of the title compound of Example 5 (80 mg, 0.326 mmol) in anhydrous DMF 5 mL and stir the so-formed reaction mixture for 5 minutes. Add dimethyl sulfate (0.5 mL, 0.528 mmol) and stir the so-formed mixture at 20° C. for 25 minutes. Add water (3 mL) thereto and remove the precipitated solid by filtration. Wash the solid with water (3×10 mL), hexane (2×10 mL) and dry it at 60° C. at a 0.2 mm Hg vacuum to provide the title compound, 16a (80 mg, 98% of theory).

Example 7

6-Methoxy-4-Methylsulfinyl-3-Methyl-1H-Pyrazolo[3,4-b]Quinoline (20a)

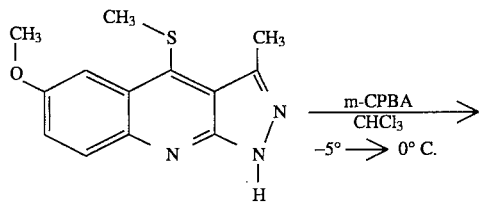

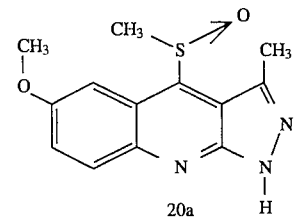

20a

To a stirred suspension of the product of Example 6 (15 g, $5.76\times10^{-2}$ mol) in methylene chloride (300 mL) at −5° C. was added, m-chloroperoxybenzoic acid ("m-CPBA", 80%, 13.2 g, 6.14×10−2). A solution was immediately formed and after 15 minutes a solid precipitated. The reaction mixture was stirred an additional 10 minutes at 0° C. Filter the precipitated solid and wash it with cold methylene chloride (10 mL), hexanes (2×10 mL). Dry the washed solid at 50°

C. and 0.2 mm Hg to produce the 4-sulfinyl-6-methoxy-3-methyl-1H-pyrazolo [3,4-b] quinoline. Purify the solid by recrystallization from methanol to give the title compound, 20a, as yellow needles; (11.2 g, 70.44% of theory)

mp: 250° to 252° C.;

M.S. EI M$^+$: 275

Example 8

2-[(6-Methoxy-3-Methyl-1H-Pyrazolo[3,4-b]-Quinoline-4-yl)Thio]-Propionic Acid, Sodium Salt (21a)

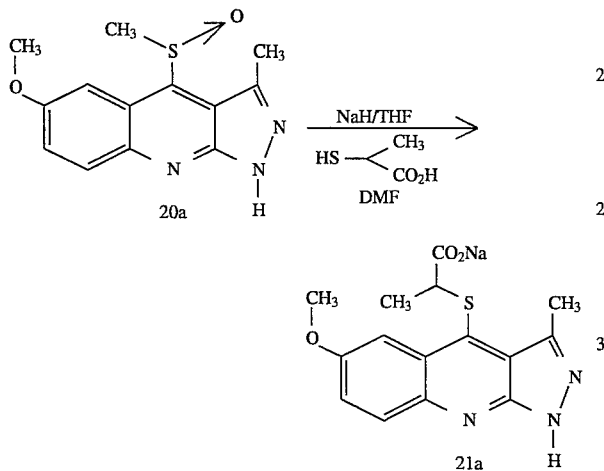

a) Add sodium hydride (60% in oil, 50 mg, 1.31 mmol) to a solution of thiolactic acid (0.5 mL, 5.62 mmol) in anhydrous tetrahydrofuran (THF) and stir the so-formed reaction mixture for 10 minutes. Add the 6-methoxy-4-methylsulfinyl quinoline (20a) prepared in accordance with the procedure of Example 7 (130 mg, 0.471 mmol) dissolved in anhydrous DMF (3 mL) and heat the so-formed solution at reflux for 1 hour. Cool the reaction mixture and add water (15 mL) and 2N HCl (ca 5 mL) thereto and allow the so-formed reaction mixture to stand overnight. Remove the precipitated solid by filtration and wash the filtered solid with water (10 mL) and dry it at 60° C. and a vacuum of 0.2 mm Hg to provide the acid (120 mg, 8.05% of theory).

b) Add sodium bicarbonate (29.1 mg, 0.346 mmol) to a suspension of the acid of Example 8(a) in water (10 mL) and acetonitrile (10 mL). Stir the so-formed solution for 10 minutes. Remove the solvents by evaporation to provide a residue. Dissolve the so-formed residue in methanol (MeOH, 15 mL) and filter the so-formed solution. Concentrate to solution to 5 mL, add diethylether (25 mL) and filter the so-formed precipitate. Wash it with diethylether (2×10 mL) and dry the solid at 60° C. and a vacuum on 0.2 mm Hg to provide the title substance, (21a) a sodium salt as a yellow powder (90 mg, 90% of theory). M.S. (EI, M$^+$) 317.

Example 9

6-Methoxy-4-(2-Phenylethylthio)-3-Methyl-1(H)-Pyrazolo[3,4-b]Quinoline

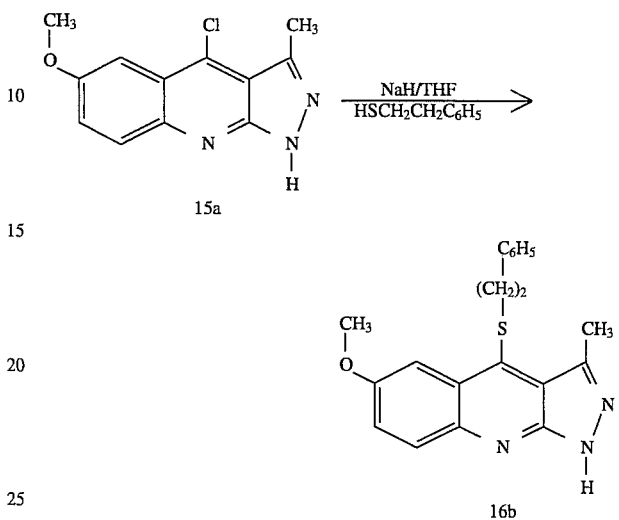

Add sodium hydride (60% in mineral oil, 100 mg, 2.6 mmol) to a solution of 2-phenylethylmercaptan (30 mg, 2.17 mmol) in anhydrous THF (50 mL). Stir the so-formed solution for 30 minutes. Add the 4-chloro-6-methoxyl-3-methyl-1H-pyrazolo [3,4-b] quinoline (15a) of Example 3 (500 mg, 2.02 mmol) to the reaction mixture and heat the so-formed reaction mixture at reflux temperature overnight. Cool the reaction mixture to 40° C., add water (20 mL) thereto, and recover the precipitated solid by filtration. Wash the solid with water (20 mL) and dry it at 60° C. at a vacuum of 0.2 mm Hg. Chromatograph the crude product on a silica gel column; use 5% MeOH-CH$_2$Cl$_2$ as the eluiant to produce a yellow powder. Crystallize the yellow solid from methanol-acetone to produce the title compound as yellow leaflets (520 mg, 65% of theory).

M.S. (EI, M$^+$) 349.

Molecular Formula: C$_{20}$H$_{19}$N$_3$OS;

Calc: C:68.74%, H:5.48%, N:12.02%; Found C:68.16%, H:5.55%, N:12.00%.

Example 10

To prepare the compounds of formula 1a, listed in the Table below, follow the procedure of Example 9 except substitute for the mercaptan in Example 9, an equivalent quantity of the mercaptan listed in Column B and for the 6-methoxy-pyrazoloquinoline substitute an equivalent amount of the appropriate 6-substituted pyrazoloquinoline of Example 4 listed in Column A. The mercaptans in Column B are commercially available from Aldrich Chemical Co., Milwaukee, Wisc. 53233 or readily obtainable by standard synthetic techniques.

TABLE I

Product:

$$\text{1a: quinoline fused with pyrazole, bearing } S-R_2 \text{ at C-4, } CH_3 \text{ at C-3, } R_3 \text{ on benzene ring, and } R^1 \text{ on pyrazole N}$$

| Example | A (Example #) | B | R₁ | R₂ | R₃ |
|---|---|---|---|---|---|
| 10a | 3 | HS–C₆H₄–NH₂ | H | C₆H₄NH₂ | 6-CH₃O |
| 10b | 3 | HS–C₆H₅ | H | C₆H₅ | 6-CH₃O |
| 10c | 4a | HS–C₆H₅ | H | C₆H₅ | 6-F |
| 10d | 4b | HS–C₆H₅ | H | C₆H₅ | 6-CH₃ |
| 10e | 4c | HS–C₆H₅ | H | C₆H₅ | 6-CF₃ |
| 10f | 4d | HS–C₆H₅ | H | C₆H₅ | 6-Cl |
| 10g | 3 | HSCH₂C₆H₅ | H | CH₂C₆H₅ | 6-CH₃O |
| 10h | 3 | HSCH₂-(2-furyl) | H | CH₂-(2-furyl) | 6-CH₃O |
| 10i | 3 | HS-(1-methylimidazol-2-yl) | H | 1-methylimidazol-2-yl | 6-CH₃O |
| 10j | 4a | HS-(1-methylimidazol-2-yl) | H | 1-methylimidazol-2-yl | 6-F |
| 10k | 3 | HS-(4-methylpyrimidin-2-yl) | H | 4-methylpyrimidin-2-yl | 6-CH₃O |
| 10l | 4a | HS-(4-methylpyrimidin-2-yl) | H | 4-methylpyrimidin-2-yl | 6-F |
| 10m | 3 | HS-(2-furyl) | H | 2-furyl | 6-CH₃O |
| 10n | 3 | HSCH₂CH=CH₂ | H | CH₂CH=CH₂ | 6-CH₃O |
| 10o | 3 | HSCH₂CH₂NMe₂ | H | CH₂CH₂NMe₂ | 6-CH₃O |
| 10p | 3 | HS–C₆H₄–CH₃ | H | C₆H₄–CH₃ | 6-CH₃O |

TABLE II

Mass Spectral and Microanalysis Data

[Structure: 6-methoxy-quinoline fused with pyrazole, with X substituent at position 4 and CH3 at position 3]

| Example No. | Mass No (MS, EI, M+) | X | | % C | | % H | | % N |
|---|---|---|---|---|---|---|---|---|
| 10k | 337 | –S–(4-methylpyrimidin-2-yl) | Calculated: Found: | 60.51 60.48 | Calculated: Found: | 4.48 4.31 | Calculated: Found: | 20.75 20.98 |
| 10b | 321 | –S–phenyl | Calculated: Found: | 67.26 67.31 | Calculated: Found: | 4.70 4.63 | Calculated: Found: | 13.07 13.13 |
| 10p | 335 | –S–(4-methylphenyl) | Calculated: Found: | 68.03 68.07 | Calculated: Found: | 5.10 4.87 | Calculated: Found: | 12.53 12.53 |
| 10g | 335 | –SCH2–phenyl | Calculated: Found: | 68.03 67.88 | Calculated: Found: | 5.10 4.95 | Calculated: Found: | 12.53 12.50 |
| 10h | 325 | –SCH2–furan | Calculated: Found: | 62.75 62.92 | Calculated: Found: | 4.64 4.11 | Calculated: Found: | 12.91 12.82 |
| 10n | 285 | –SCH2CH=CH2 | Calculated: Found: | 63.13 63.03 | Calculated: Found: | 5.29 5.48 | Calculated: Found: | 14.72 14.43 |
| 10a | 336 | –S–(4-aminophenyl) | Calculated: Found: | 64.26 64.41 | Calculated: Found: | 4.79 4.92 | Calculated: Found: | 16.65 16.22 |

Example 11

1-Acetyl- and 1(H)-6-Methoxy-4-Thioxo-3-Methyl-1(H)-Pyrazolo[3,4-b] 9(H) Quinoline (19a and b)

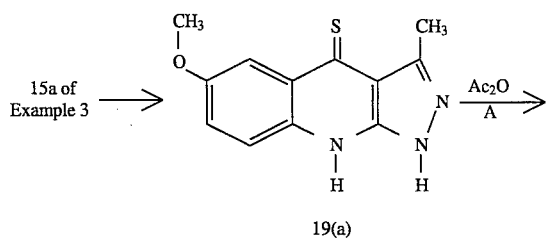

19(a)

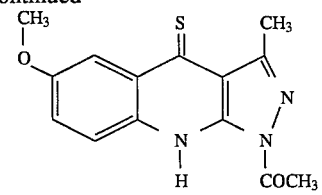

19b a) 6-Methoxy-4-Thioxo-3-Methyl-1(H) Pyrazolo[3, 4-b]-9(H)-Quinoline. 19(a)

Add sodium hydride (60% in mineral oil, (200 mg, 5.25 mmol) to a suspension of the 4-chloropyrazolo[3,4-b]quinoline, 15a, (400 mg, 1.62 mmol) prepared in accordance with Example 3 and sulfur (0.25 g, 7.5 mmol) in anhydrous THF (50 mL) and stir the so-formed reaction mixture at reflux for one hour. Cool the reaction mixture and remove the solvents at reduced pressure to produce a residue. Dissolve the residue in 1N HCl (15 mL) and methanol (10 mL) and stir the so-formed mixture at reflux for 2 hours. Allow the reaction mixture to cool to room temperature. Remove the precipitated solid by filtration and wash it with water (10 mL). Dry the solid at 60° C. under 0.1 mm Hg vacuum to provide the title compound 19(a) (250 mg, 63.13% of theory).

b) 1-Acetyl-6-Methoxy-4-Thioxo-3-Methyl-1(H) Pyrazolo-[3,4-b]-9(H)-Quinoline (19b)

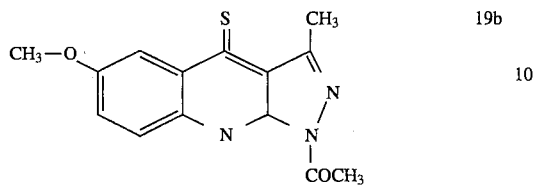

19b

Add para-toluenesulfonic acid monohydrate (3.03 g, 15.7 mmol) to a suspension of the 6-methoxy-4-thioxo-pyrazolo quinoline 19(a) (6.0 g, 24.4 mmol) of Example 11(a) in acetic anhydride (200 mL) at 20° C. and heat the so-formed reaction mixture at reflux for one hour. Allow the resulting reaction mixture to cool to room temperature over a 3 hour period. Remove the precipitated crystalline solid by filtration and wash it with acetic anhydride (5 mL) water (3×10 mL). Dry the crystals at 60° C. under a vacuum. Crystallize the dried solid from DMF-acetone to produce the title product 19b of Example 11b as a solid (6.3 g, 90% of theory).

Example 12

1-Acetyl- and 1H,-3,6-Dimethyl-4-Thioxo-9(H)-Pyrazolo[3,4-b]Quinoline (19c and d)

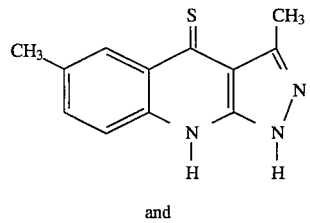

19c and

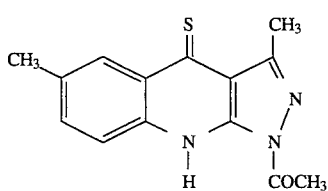

19d

Follow the procedures of Example 11(a) and (b) except substitute an equivalent quantity of the 6-methyl-4-chloro-pyrazolo [3, 4b] quinoline of Example 4(b) for the 6-methoxy-4-chloro-pyrazolo [3,4-b] quinoline to obtain the title compounds.

EXAMPLES 13

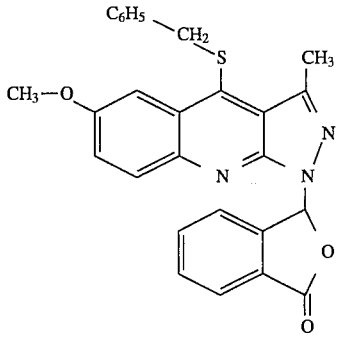

16g

A) Preparation of 1-bromophthalide

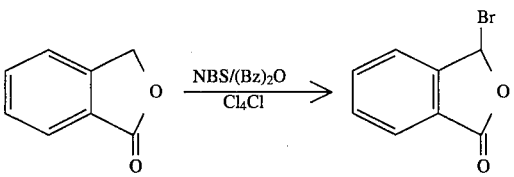

Add N-bromosuccimide (NBS) (9.2 g, 51.6 mmol) and benzoyl peroxide [(Bz)$_2$O] (5 mg, 2.06×10$^{-5}$ mol) to a suspension of phthalide (5.79 g, 43.1 mmol) in Cl$_4$Cl (300 mL). Heat the so-formed reaction mixture at reflux temperature for 3 hours. Cool the reaction mixture to 20° C. and add water (200 mL). Separate the organic layer and wash it with saturated aqueous sodium bicarbonate (200 mL). Dry the organic layer over magnesium sulfate, filter and evaporate the organic filtrate to produce a white solid. Triturate the white solid with hexanes to produce the title product as a white powder (6.5 g., 70.6% of theory).

B)

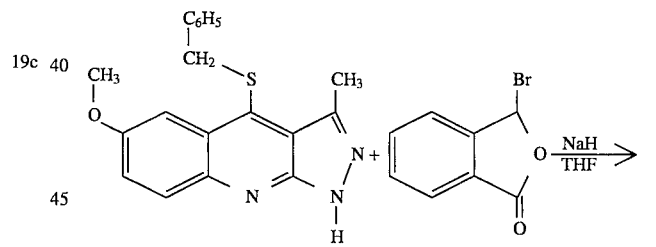

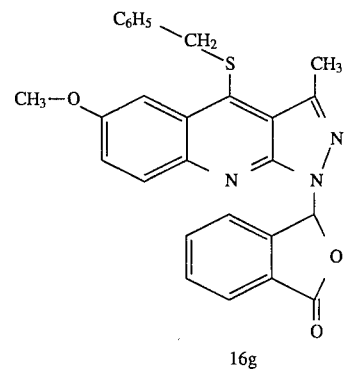

16g

Add sodium hydride (60% in oil, 71 mg, 1.77 mmol) to a suspension of 6-methoxy-4-benzylthio-3-methyl-1(H) pyrazolo-[3,4-b] quinoline (500 mg, 1.48 mmol of the product of Example 10 g) in anhydrous THF (10 mL). Stir the so-formed reaction mixture at 20° C. for 30 minutes. Add a stoichiometric excess of 1-bromophthalide produced in step A. Stir the so-formed reaction mixture overnight. Evaporate the solvent and extract the residue with methylene chloride (300 mL). Wash the organic layer with water (200 mL) and dry it over magnesium sulfate. Filter the organic layer and remove the organic solvent at reduced pressure to produce a solid. Chromatograph the solid on silica gel and elute the column with 30% (v/v) EtoAc: hexanes to produce the product of formula 16 g as a white powder. (500 mg, 70.52% of theory) MP 168°–170° C.; MS (MS/CI m/e M=1 (468); Molecular Formula: $C_{27}H_{21}N_3O_3S$: Calc: C, 69.36%; H, 4.53%; N, 8.98%; Found: C, 69.68% ;H, 4.68%; N, 8.90%.

Example 14

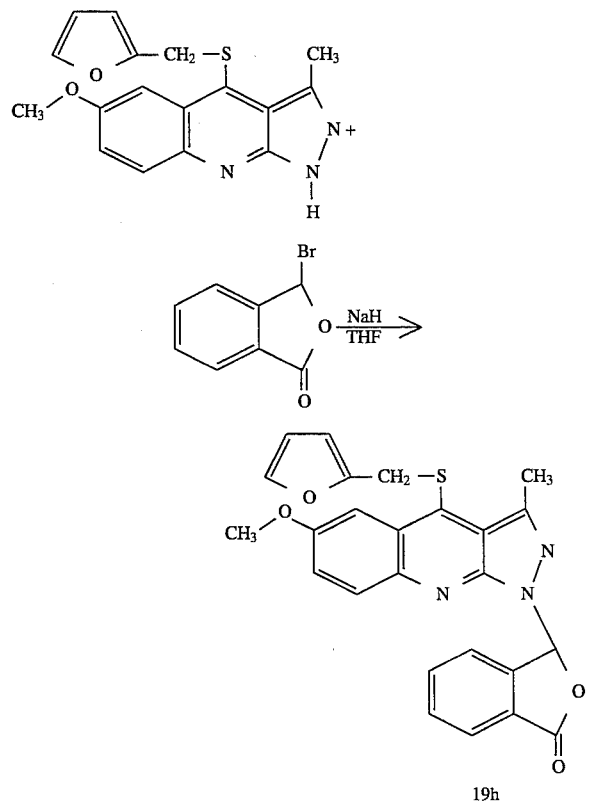

Follow the procedure of Example 13 except substitute an equivalent quantity of 6-methoxy-4-furanylmethylthio-3-methyl-(H)pyrazolo-[ 3,4-b]quinoline of Example 10h for the 4-benzylthio of Example 10g. Chromatograph the crude solid on a silica gel column and elute the column with 25% (v/v) EtoAC in hexanes to provide 420 mg of the title product, 19h, (69.4% of theory). MS: CI, (M+1) 457: mp 165°–166° C.

Example 15

2-[(6-Methoxy-3-Methyl-1H-Pyrazolo[3,4-b]-Quinolin-4-yl)Thio]-[3-(2-Oxo-1-Pyrrolidinyl)-Propyl]-2-Methyl Acetamide (21d)

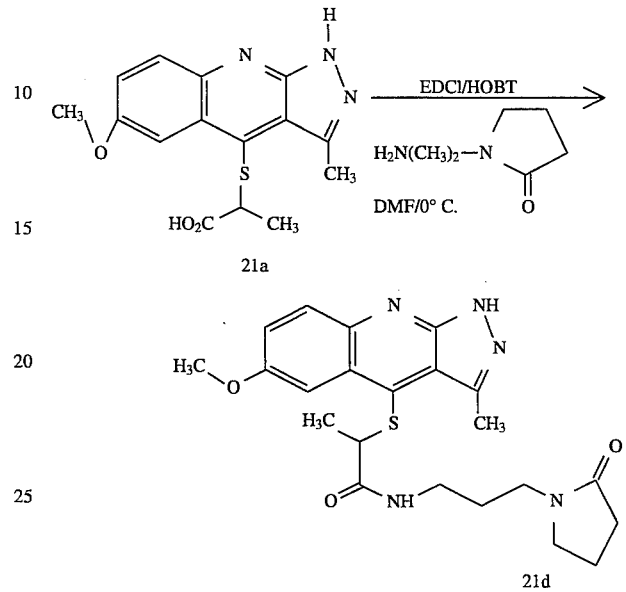

Add 1-(3-dimethylaminopropyl)-3-ethylcarbodiimide hydrochloride (EDCl) 140 mg, $7.33 \times 10^{-4}$M) and 1-hydroxybenzotriazole (HOBT,) monohydrate (120 mg, $8.88 \times 10^{-4}$M) to a solution of 2-[(6-methoxy-3-methyl- 1 H-pyrazolo-[3,4-b]quinoline-4-yl)thio]-propionic acid of Example 8 (150 mg, $4.73 \times 10^{-4}$M) in anhydrous DMF, 10 mL) at 0° C. Stir the so-formed mixture at 0° C. for 40 minutes. Add 1-(3-aminopropyl)- 2-pyrrolidinone (0.3 mL, $23.2 \times 10^{-4}$M) and stir the mixture at 20° C. overnight. Evaporate the solvent. Add water (20 mL), and methylene chloride (100 mL). Separate the organic layer separated, wash it with brine (20 mL) and dry it over magnesium sulfate. Filter and evaporate the filtrate to yield an oil. Add acetone (5 mL) hexanes (10 mL) and place solution in a refrigerator at 0° C. overnight. Filter the precipitated solid, wash it with hexanes (10 mL) and dry it at 60° C./0.2 mm to give the title compound, 21d, as a yellow solid; mp 221°–222° C. Molecular formula: $C_{22}H_{27}N_5O_3S$: Calc: C:59.84%; H:616%, N:15.86%; Found: C:59.42%; H:5.83%; N:15.69%.

Example 16

2-[(6-Methoxy-3-Methyl-1H-Pyrazolo[3,4-b]-Quinolin-4-yl)Thio]-[2-(4-Morphinyl) Ethyl]-2-Methyl Acetamide (21e)

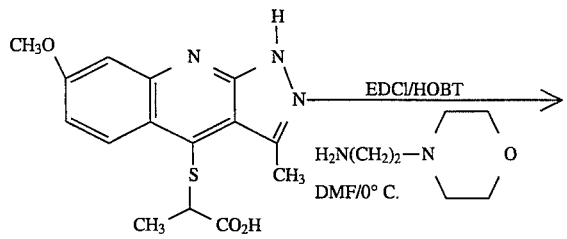

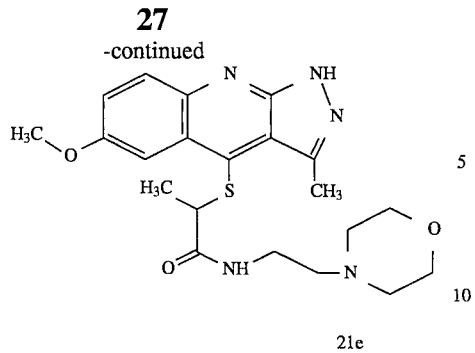

21e

Follow the procedure of Example 15 except for 1-(3-aminopropyl)- 2-pyrrolidinone, substitute an equivalent quantity of 1-(2-aminoethyl)morpholine to produce the title compound, 21e, as a yellow solid mp 219°–220° C.; MS (FAB) M+1, 430; molecular formular $C_{21}H_{27}N_5O_3S$.

Example 17

4-Acetylthio-6-Methoxy-3-Methyl-1H-Pyrazolo [3,4-b] Quinoline (22a)

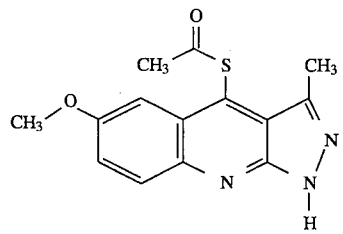

22a

Add acetic anhydride (1.0 mL, 10.5 mmol) to a suspension of the 6-methoxy-4-thioxo-3-methyl-1(H)-pyrazolo-[3,4-b] 9(H)quinoline (200 mg, 0.816 mmol) of Example 11(a) in anhydrous pyridine (10 mL) at room temperature. Stir the so-formed reaction mixture for 15 minutes. Remove the precipitated solid by filtration and wash it with water (10 mL). Dry the solid at 60° C. under a vacuum of 0.1 mm Hg to produce the title compound as a yellow solid (200 mg).

Example 18

6-Fluoro-3-Methyl-1(H)-Pyrazolo[3,4-b]Quinolin-4-Thione and 4,4'-Thio Bis[6-Fluoro-3-Methyl-1H-Pyrazolo[3,4-b]Quinoline]

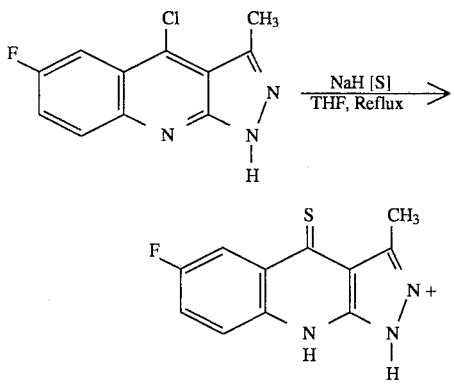

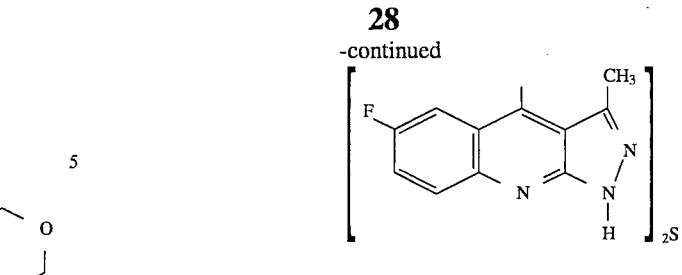

Add NaH (60% in oil, 150, 3.75 mmol) to a suspension of 6-fluoro-4-chloro-3-methyl-1[H]pyrazolo[3,4-b]quinoline of Example 4a (350 mg 1.48 mmol) and sulfur (60 mg, 1.875 mmol) in anhydrous THF (30 mL) and heat the so-formed reaction mixture at reflux for 4 hours. Cool it to room temperature and add water (20 mL). Filter the precipitated solid, wash it with water (2×20mL). Purify the solid by crystallization from DMF/water to provide 60 mg of 4,4'-thio bis[6-fluoro- 3-methyl-1(H)Pyrazolo[3,4-b]quinoline as a yellow powder (9.3% of theory); M.S. El (m/e, 432); molecular formula: $C_{22}H_{14}F_2N_6S$.

Combine the filtrate washings and mother liquors and evaporate to remove the THF. Acidify the solid residue so-formed with 1N HCl. Wash the solid with water (10 mL) and dry it at 60° C. and 0.2 mm Hg. Purify the solid by crystallization from MEOH:acetone to provide 260 mg of 6-fluoro-3-methyl-1(H)pyrazolo[3,4-b]quinoline 4-thione as a red crystalline solid. (75% of theory). M.S. CEI, (m/e 233); molecular formula $C_{11}H_8FN_3S$.

Example 19

4,4'Thiobis[6-methoxy-3-methyl]1[H]Pyrazolo-[3,4-b]Quinoline

Follow the procedure of Example 18 except substitute an equivalent quantity of the compound 15a prepared in accordance with the procedures of Example 3 for the 6-fluoro-pyrazolo (3,4-b) quinoline to obtain the title compound as a yellow powder.

Example 20

4,4'-Thiobis[6-Methoxy-3-Methyl-1-Acetyl-1H-Pyrazolo [3,4-b]Quinoline]

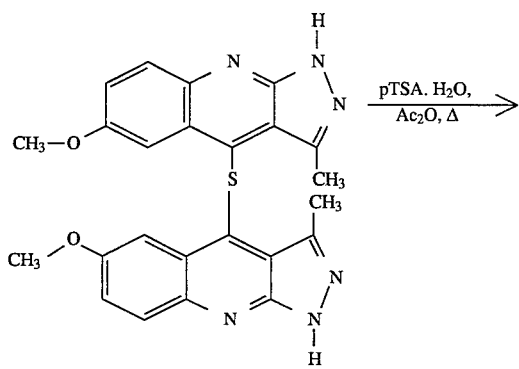

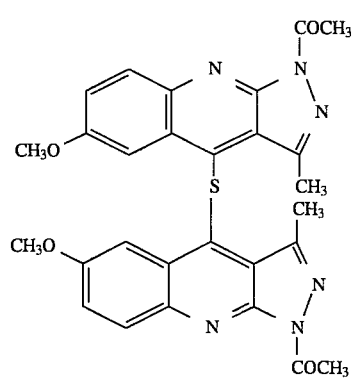

Add toluene sulfonic acid ("pTSA") monohydrate (3.0 g 1.57 mmol) to a suspension of the product of Example 19 (6:0 g 13.1 mmol) in acetic anhydride (Ac₂0, 300 mL). Heat the so-formed mixture at reflux temperature (125° C.) for 1 hour. Cool the reaction mixture to 40° C. and allow crystals to form. Maintain temperature of the reaction mixture at 40° C. for ½ hr. Filter the crystalline solid, wash it with Ac₂0 (10 mL), water (3×30 mL) and dry the washed solid at 60° and 0.2 mm Hg to provide 6.1 g of the title compound as a pale yellow needles. Molecular Formula: $C_{28}H_{24}N_6O_4S$;

Calc: C: 58.53%; H: 4.56%; N: 14.62% Found: C:58.57%; H:4.39%; N:14.64%.

X-Ray spectrum confirms the structure listed above.

Example 21

3-[(6-Methoxy-3-Methyl-1H-Pyrazolo [3,4-b] Quinolin-4-yl) Thiol]-1,2-Propanediol

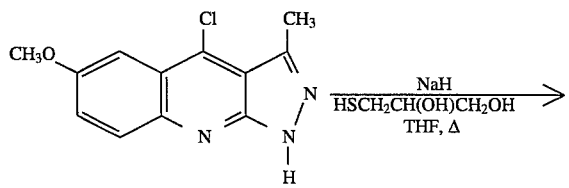

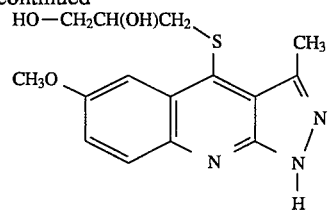

Add NaH (60% suspension in oil, 60 mg 1.50 mmol) to a suspension of 3-mercapto-1,2-propanediol (Aldridch, 1.0 mL, 11.9 mmol) in anhydrous THF (60 mL) and stir the so-formed reaction mixture at 20° C. for ½ hr. Add 4-chloro-6-methoxy-3-methyl-1[H] prazolo [3,4-b] quinoline of Example 3 (300 mg., 1.21 mmol and heat the stirred reaction mixture so-formed at reflux temperature for 5 hours. Cool the reaction mixture to room temperature and evaporate the solvent. Add water (25 mL) and extract with methylene chloride (70 mL). Separate the organic layer, wash it with saturated brine (40 mL) and dry it over magnesium sulfate. Filter and evaporate to produce an oil. Chromatograph the oil on silica gel and elute the column with 10% (v/v) MEOH: CH₂Cl₂ to produce the title compound as a yellow powder, mp 217°–219° C.; MS (FAB; M+1 320); Molecular formula $C_{15}H_{17}N_3O_3S$;

Calc: C: 56.41%; H: 5.36%; N: 13.16%; Found: C: 55.97%; H: 5.32%; N: 12.87%.

The compounds of the present invention wherein $R_9$ is $(C_2-C_8)$alkyl may be prepared by substituting the appropriate

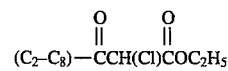

for compound 13 in Example 2a. The compound of the formula (30)

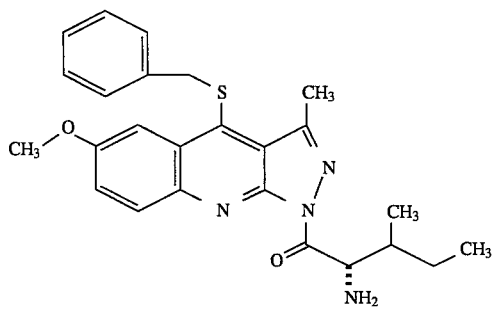

may be prepared by methods analogous to those set forth in the following example:

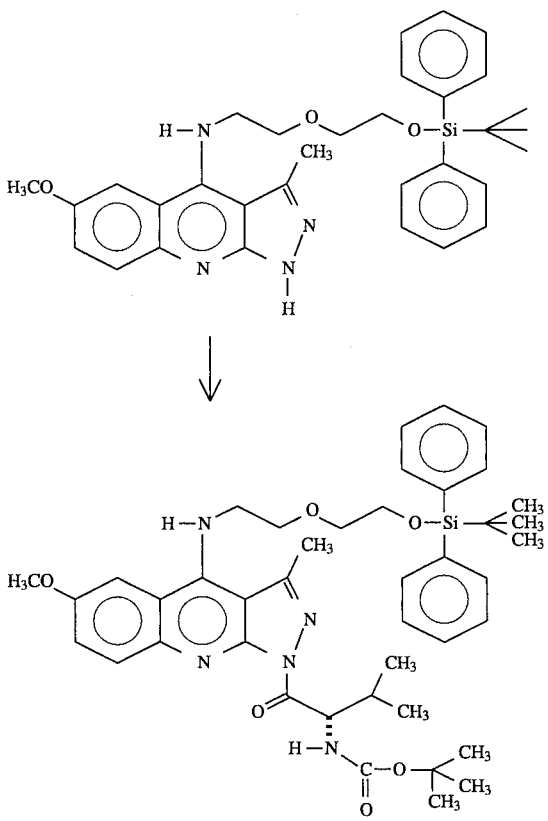

Sodium hydride (60% in oil, 200 mg, 5.0 mmol) was added to a solution of 2-[[2-[(6-methoxy-3-methyl-1H-pyrazolo-[3,4-b] quinolin-4-yl)amino] ethyl]oxy]ethyl] oxy]-[1,1-dimethylethyl-diphenylsilane] (1.0 g, 1.80 mmol) in tetrahydrofuran (20 ml, anhydrous) at 20° C. The resulting reaction mixture was stirred for 20 minutes. t-butoxy carbonyl-L-valine hydroxysuccinimide ester (1.2 g, 3.82 mmol) was then added. The reaction was stirred for 4 hours at ambient temperature, and the solvent was evaporated.

The residue was extracted with methylene chloride (200 ml), washed with water (100 ml), dried (magnesium sulfate), filtered and the solvent was evaporated to yield an oil which was chromatographed on silica gel with 1/1 (v/v) ethyl acetate/hexanes as the eluant to yield the product as a white foam. MS (FAB m/e M+1 (754). The starting materials which would be used in making a compound of formula (30) are as follows:

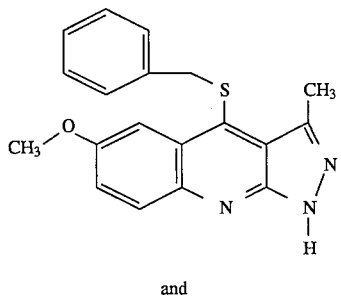

and

-continued

[structure]

Other modifications within the skill of the art are also considered within the scope of the present invention.

What is claimed is:

1. A compound represented by formula 2

[structure 2]

and pharmaceutically acceptable salts thereof wherein $R_1$ equals H, $(C_2-C_8)$alkanoyl,

[structure]

or $-CH_2O-(C_2-C_8)$alkanoyl $R_2$ is H, $(C_1-C_8)$alkyl, $(C_2-C_8)$alkanoyl, $-(C_2-C_6)$alkylene, $-(CHR_4)_s-N(R_5)_2$, $-(CHR_4)_s-CO_2M$,

[structures]

$R_3$ is $OR_5$, F, Cl, Br, I, $CF_3$ or, $(C_1-C_8)$alkyl;

$R_4$ is H or $(C_1-C_8)$alkyl;

$R_5$ is H, $(C_1-C_8)$alkyl or $(C_2-C_8)$alkanoyl;

$R_6$ is $R_3$, $N(R_5)_2$, $(C_2-C_7)$alkanoyl or H;

$R_9$ is $(C_1-C_8)$alkyl;

M is H or a pharmaceutically acceptable cation;

q is 2 or 3;

s is 1, 2, 3, or 4; and t is 0, 1, 2, or 3; and when $R_1$ is H, $R_3$ is not methyl.

2. A compound of claim 1 wherein $R_3$ is 6-$(C_1-C_8)$alkyl-O-.

3. A compound of claim 1 wherein $R_3$ is 6-$CH_3$-O-.

4. A compound of claim 1 wherein $R_2$ is

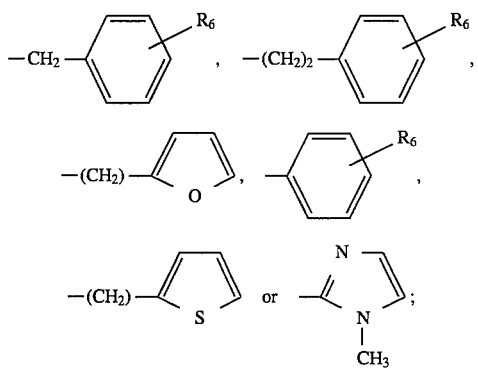

$R_1$ is H or

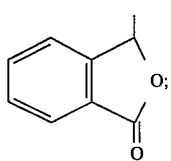

and n is o.

5. A compound of claim 1 wherein in formula 2, $R_3$ is 6-$CH_3O$ and $R_2$ is

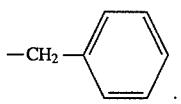

6. A compound of claim 1 wherein in formula 2, $R_9$ is $CH_3$.

7. The compound according to claim 1 of the formula

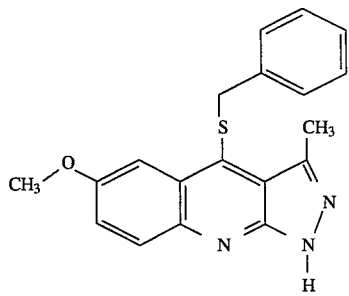

or a pharmaceutically acceptable salt thereof.

8. The compound according to claim 1, of the formula

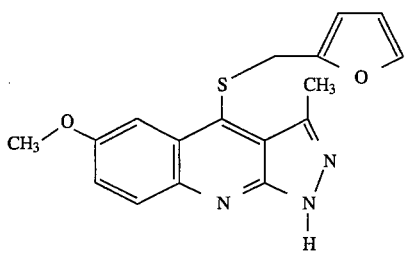

or a pharmaceutically acceptable salt thereof.

9. A pharmaceutical composition for treating patients afflicted with a herpes group virus which comprises an anti-herpes effective amount of a compound of formula 2 of claim 1 and a pharmaceutically acceptable carrier therefor.

10. A method of treating a patient afflicted with a herpes group virus which comprises administering to said patient an anti-herpes effective amount of a compound of formula 2 of claim 1.

11. A compound of the formula

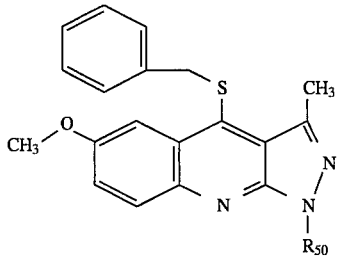

wherein $R_{50}$ is the residue of a naturally occuring α-amino acid, or a pharmaceutically acceptable salt thereof.

12. The compound according to claim 11 of the formula (30)

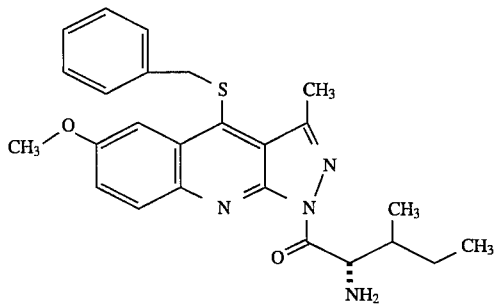

or a pharmaceutically acceptable salt thereof.

* * * * *